United States Patent [19]
Pellico

[11] Patent Number: 5,928,628
[45] Date of Patent: Jul. 27, 1999

[54] TWO-COMPONENT DENTAL BLEACHING SYSTEM AND METHOD

[76] Inventor: Michael A. Pellico, 3024 Military Ave., Los Angeles, Calif. 90272

[21] Appl. No.: 08/957,008

[22] Filed: Oct. 23, 1997

[51] Int. Cl.$^6$ .............................. A61K 7/16; A61K 7/20
[52] U.S. Cl. ................................ 424/49; 424/53
[58] Field of Search .................... 424/49, 53, 687, 424/688; 514/900, 901, 902

[56] References Cited

U.S. PATENT DOCUMENTS

| | | |
|---|---|---|
| Re. 34,196 | 3/1993 | Munro . |
| 4,528,180 | 7/1985 | Schaeffer . |
| 4,839,156 | 6/1989 | Ng et al. . |
| 4,980,152 | 12/1990 | Frazier et al. . |
| 5,059,417 | 10/1991 | Williams et al. . |
| 5,186,926 | 2/1993 | Williams et al. ............ 424/53 |
| 5,376,006 | 12/1994 | Fischer ..................... 433/215 |
| 5,401,495 | 3/1995 | Murayama ................. 424/49 |
| 5,425,953 | 6/1995 | Sintov et al. . |
| 5,631,000 | 5/1997 | Pellico . |

OTHER PUBLICATIONS

H. Frysh, et al. (Journal of Esthetic Dentistry, vol. 7, No. 3, pp. 130–133, 1995).

*Primary Examiner*—Thurman K. Page
*Assistant Examiner*—Sharon Howard
*Attorney, Agent, or Firm*—Donald Diamond

[57] ABSTRACT

A two-component dental bleaching system is provided wherein the components are adapted to be admixed and applied to the teeth from a dental bleaching tray. One component comprises a dental peroxide gel having a pH from about 4 to about 7 and the other component comprises an orally compatible alkaline gel having a pH from about 9 to about 13. The admixing of the components provides a dental bleaching gel having a pH from about 8.5 to about 11 to thereby increase the rate of release of active oxygen and accelerate the bleaching action.

4 Claims, No Drawings

TWO-COMPONENT DENTAL BLEACHING SYSTEM AND METHOD

FIELD OF THE INVENTION

This invention relates to dental bleaching compositions and, more particularly, to a two-component dental bleaching system wherein the components are adapted to be admixed and applied to the teeth from a dental bleaching tray to achieve an accelerated bleaching action.

BACKGROUND OF THE INVENTION

In that aspect of aesthetic dentistry which relates to self-administered use of in-home tooth whitening compositions, the dental patient is provided with a custom-fitted dental try having selectively enlarged tooth treating compartments which are adapted to receive a whitening gel that is dispensed from a syringe. The dental tray, with its gel content, is unobtrusively and advantageously worn by the patient at night and while the patient sleeps. This treatment is repeated for a sufficient period of time to effect the tooth bleaching and whitening process.

It is disclosed in the prior art that hydrogen peroxide, carbamide peroxide (urea peroxide) and other peroxides can be used as the whitening agents in the formulation of tooth whitening gels. The prior art also discloses that carboxy-polymethylene (Carbopol) and poloxamer (Pluronic) as well as other thickeners can be used as the gelling agent in the preparation of peroxide gels. The gels can be water based or anhydrous.

U.S. Reissue Pat. No. 34,196 (Munro, 1993) discloses an anhydrous dental brightening gel comprising carbamide peroxide in a water-free gel for sustained release and which is applied to the teeth from a dental bleaching tray.

U.S. Pat. No. 5,631,000 (Pellico, 1997) discloses an anhydrous tooth whitening gel comprising carbamide peroxide dispersed in a substantially anhydrous gelatinous carrier containing, for example, neutralized carboxypolymethylene, hydroxypropyl cellulose, propylene glycol, polyethylene glycol and glycerin in an amount that does not exceed about 10 wt. % of the gel composition.

U.S. Pat. No. 5,098,303 (Fisher, 1992), U.S. Pat. No. 5,234,342 (Fisher, 1993), U.S. Pat. No. 5,376,006 (Fisher, 1994) and U.S. Pat. No. 5,409,631 (Fisher, 1995) disclose tooth bleaching and whitening gels formulated with carbamide peroxide, water, glycerin, carboxypolymethylene and sodium hydroxide wherein the concentration of carboxypolymethylene is so selected as to provide the gel composition with a tackiness or stickiness.

U.S. Pat. No. 5,401,495 (Murayama, 1992) discloses an aqueous dental bleaching gel comprising hydrogen peroxide, a gelling agent such as Carbopol (carboxypolymethylene), or polyoxyethylene polyoxypropylene block copolymers (poloxamer) as described in U.S. Pat. No. 3,639,574 (Schmolka, 1972), and a thickener identified as hydroxyethyl cellulose gum, hydroxypropyl cellulose gum, or carboxymethyl cellulose.

U.S. Pat. No. 5,425,953 (Sintov, et al., 1995) discloses a sustained-release, film forming, dental bleaching composition comprising a cellulosic polymer such as hydroxypropyl cellulose or carboxymethyl cellulose, a peroxy compound such as hydrogen peroxide, carbamide peroxide or sodium peroxyborate monohydrate, a stabilizing additive such as calcium disodium ededate, and a vehicle such as water, ethyl alcohol or a combination thereof.

U.S. Pat. No. 4,839,156 (Ng, et al., 1989), which is incorporated herein by reference, discloses a hydrogen peroxide dental gel containing hydrogen peroxide, polyethylene glycol humectant, a non-ionic surfactant such as Tween 20, flavoring and sweetening ingredients, and from about 18–25% by weight of polyoxyethylene polyoxypropylene block copolymer (Pluronic/Poloxamer) gelling agent.

U.S. Pat. No. 4,980,152 (Frazier, et al., 1990) discloses an aqueous dental gel comprising hydrogen peroxide or carbamide peroxide, a thickening agent such as Carbopol brand carboxypolymethylene in an amount from about 0.5 to about 6.5% by weight and/or a non-ionic surfactant such as Pluronic F127 brand poloxamer in an amount from about 10 to about 28% by weight, together with a fluoride, cellulosic thickener, buffering agent, glycerine, preservatives and water.

U.S. Pat. No. 5,059,417 (Williams, et al., 1991) discloses a clear dental gel containing a peroxygen compound such as sodium perborate, persilicate, perphosphate or hydrogen peroxide, poloxamer gelling agent and glycerol in an amount to stabilize the gel against low temperature liquification.

U.S. Pat. No. 4,528,180 (Schaeffer, 1985), U.S. Pat. No. 4,687,663 (Schaeffer, 1987) and U.S. Pat. No. 4,849,213 (Schaeffer, 1989) disclose a two-component dental product wherein a first component comprises a dental gel containing, for example, hydrogen peroxide, water, Carbopol 934, Pluronic F127, hydroxypropyl methyl cellulose and sodium hydroxide, and the second component comprises an aqueous dental paste containing, for example, sodium bicarbonate, sodium chloride, glycerin, propylene glycol, thickener and polishing agent. The first and second components are adapted to be simultaneously dispensed onto a toothbrush for application to the teeth. The patentee points out that the two-component system provides the oral care benefits achieved through the combination of hydrogen peroxide, sodium bicarbonate and table salt and overcomes the hydrogen peroxide dissociation that would arise through the unitary packaging of these ingredients, since hydrogen peroxide and sodium bicarbonate immediately react upon mixing.

Heretofore, dental bleaching gels adapted for use with dental bleaching trays have been formulated to provide for sustained release of the active bleaching agent over a period of several hours, including overnight use. The tray bleaching procedure typically specified that the bleaching step be repeated on a daily basis for up to about 14 days to achieve significant whitening. The long period of use required by the prior art tray bleaching procedure as well as tissue sensitivity and irritation associated with this extended procedure tends to diminish full compliance with the specified schedule for use of the bleaching gel. Accordingly, there is a need for a more rapidly acting dental bleaching gel which is adapted for use with dental bleaching trays and which reduces tissue sensitivity and irritation to thereby enhance compliance with the specified procedure for using the bleaching gels in order to achieve the most effective results.

It is disclosed in the prior art that the rate of dental bleaching with hydrogen peroxide, normally at pH 4.4, increases when the hydrogen peroxide is buffered to an alkaline pH. Howard Frysh, et al. (Journal of Esthetic Dentistry, Vol. 7, No. 3, pp. 130–133, 1995) undertook an in vitro study to determine whether alkaline peroxide solutions might be more effective in whitening teeth in a given period of time than the acidic peroxide usually employed. This study compared, for a given time interval, the bleaching effectiveness of a commercially available bleaching composition containing 35% hydrogen peroxide at pH 4.4 with a like composition buffered to pH 9.0 with an aqueous sodium hydroxide solution. The results of the study showed that, for a given time interval, alkaline hydrogen peroxide was more effective in whitening teeth than conventional acidic hydrogen peroxide by a color whitening factor in excess of 2 to 1 as measured by a Minolta Chroma Meter.

SUMMARY OF THE INVENTION

An important object of the present invention is to provide a new and improved dental bleaching system having accelerated bleaching action and reduced oral sensitivity.

Another object of this invention is to provide a two-component dental bleaching system wherein one component comprises a peroxide gel and the other component comprises an alkaline gel whereby the admixture of the components produces an alkaline dental bleaching gel having accelerated bleaching action.

A further object of this invention is to provide an two-component dental bleaching system wherein each component is stored in a separate barrel of a double barrel syringe equipped with a static mixer for dispensing admixed bleaching gel into the reservoir system of a dental bleaching tray.

These and other objects and features of the present invention are accomplished with the compositions, methods, and procedures as described herein.

In accordance with one aspect of this invention, there is provided a two-component dental bleaching system wherein the components are adapted to be admixed and applied to the teeth from a dental bleaching tray. As a first component, there is provided a dental peroxide bleaching gel having a pH from about 4 to about 7. As a second component there is provided an orally compatible alkaline gel having a pH from about 9 to about 13. The admixing of the components provides a dental bleaching gel having a pH from about 8.5 to about 11 to thereby increase the rate of release of active oxygen from the peroxide and accelerate the bleaching action.

In accordance with a second aspect of this invention, there is provided a method for bleaching teeth which comprises:

(1) concurrently extruding first and second components of a dental bleaching system through an admixing dispenser and into the reservoir system of a dental bleaching tray, (a) said first component comprising a dental peroxide gel having a pH from about 4 to about 7, and (b) said second component comprising an orally compatible alkaline gel having a pH from about 9 to about 13, (c) whereby the admixture of the first and second components provides a dental bleaching gel having a pH from about 8.5 to about 11 to thereby increase the rate of release of active oxygen and accelerate the bleaching action;

(2) placing the dental bleaching tray in the oral cavity so as to bring the admixed gel into contact with the teeth to be bleached, (3) maintaining said admixed gel in contact with said teeth for up to one hour or more per day, and (4) repeating steps one, two and three for multiple days to thereby bleach the teeth.

DETAILED DESCRIPTION

The dental bleaching compositions of this invention comprise a two-component system. As a first component, there is provided an orally compatible, peroxide bleaching gel. Diverse peroxide and peroxy compositions can be used in the preparation of the bleaching gels. However, hydrogen peroxide is particularly well suited, and is preferred, as the bleaching agent. Hydrogen peroxide is generally present in the bleaching gel in an amount from about 7% by weight to about 30% by weight, and, preferably, in an amount from about 11% by weight to about 22% by weight. A suitable source for hydrogen peroxide is the commercially available aqueous solution of hydrogen peroxide containing 50% active agent.

Gelling agents which can be used in the preparation of hydrogen peroxide gels include, for example, poloxamer, carboxypolymethalene, cellulosic gums and mixtures thereof in an amount to provide a high strength dental peroxide gel.

Poloxamer, a preferred gelling agent, is the CFTA name for polyoxyethylene polyoxypropylene block copolymers which are available under the trademark Pluronic from BASF. The polyoxyethylene polyoxypropylene block copolymers have an average molecular weight from about 3,000 to about 15,000 and preferably, from about 10,000 to about 15,000 and the polyoxyethylene portion constitutes from about 30 to about 80 and, preferably from about 70 to about 80% by weight of the molecule. Most preferred is Poloxamer 407 (Pluronic F127) which has a molecular weight from about 10,000 to about 15,000 and contains about 70% by weight of the hydrophylic polyoxyethylene moiety. Poloxamers are particularly suitable for use in this invention because of their wide pH tolerance, high compatibility with hydrogen peroxide and unique gel properties. Poloxamers are generally present in the bleaching gel in an amount from about 18 to about 29% by weight and, preferably, in an amount from about 18 to about 26% by weight. Gels prepared from Poloxamer are characterized as ringing gels which can be described as gels that have a firm jelly-like consistency such that when the gel is packed in a jar type container, and the sides of the container are tapped lightly, the gel vibrates but retains its original configuration.

The dental bleaching gels are advantageously formulated with a desensitizer in order to reduce tissue sensitivity and encourage compliance with the bleaching procedure. A preferred desensitizer is eugenol in an amount from about 0.15 to about 0.35% by weight and, preferably, in an amount from about 0.2 to about 0.4% by weight.

Adjuvants and minor use ingredients are advantageously included in the formulation to improve gel consistency and provide flavor and taste enhancements. To improve gel consistency, the dental bleaching composition can be formulated with gel modifying aliphatic polyols in an amount from about 15 to about 30% by weight. Preferred polyols include glycerine in an amount from about 8 to about 10% by weight and propylene glycol in an amount from about 10 to about 14% by weight. Xylitol, a sweetener, can be present in the gel in an amount up to about 5% by weight and a flavoring agent such as peppermint flavor can be present in the formulation in an amount up to about 0.5% by weight. The balance of the composition is deionized water.

Preparation of the peroxide gels is preferably carried out at low temperature consistent with the physical and chemical properties and gelling characteristics of the poloxamer gelling agent. In the initial steps, formulating amounts of water, xylitol, propylene glycol, glycerine and aqueous hydrogen peroxide solution are sequentially added to and stirred in a mixing vessel. The resulting solution is placed in a freezer and stored for one day at a temperature between about 0° and −14° C. The cold solution is then removed from the freezer. Poloxamer 407, in flake form, is added to and dissolved in the cold solution with stirring followed by the addition of peppermint flavor and eugenol. There is obtained a thickened product which is white in appearance. The thickened product is returned to and stored in the freezer for up to two days. At the end of this time, the admixed product is removed from the freezer as a clear liquid with a foam layer that is removed. Upon bringing the liquid phase to room temperature, it transforms to a clear gel.

As a second component of the two-component system, there is provided an alkaline gel having a pH from about 9 to about 13. Alkalinity can be provided by an alkali metal hydroxide such as sodium or potassium hydroxide, amonimum hydroxide, basic alkanolamines or equivalents thereof. The preferred alkalizing agent is potassium hydroxide and a preferred pH for the alkaline gel is from about 10 to about 12. The alkalizing agent is present in an amount to provide the alkaline gel with a pre-selected pH.

Gelling agents which can be used in the preparation of the alkaline gels include, for example, poloxamer, carboxypolymethalene, cellulosic gums and mixtures thereof in an amount to provide a high strength alkaline gel.

The preferred gelling agent for the alkaline gel is poloxamer having the chemical composition and molecular weight ranges as hereinabove described for the poloxamer gelling agent in the bleaching gel. Most preferred as the gelling agent for the alkaline gel is Poloxamer 407 (Pluronic F127). Poloxamer is generally present in the alkaline gel in an amount from about 18 to about 28% by weight and, preferably, in an amount from about 18 to about 26% by weight.

To improve alkaline gel consistency and to provide flavor and color enhancements, adjuvants and minor use ingredients are advantageously incorporated into the alkaline gel formulation. With respect to improving alkaline gel consistency, the alkaline gel can be formulated with gel modifying aliphatic polyols in an amount from about 15 to about 35% by weight. Preferred polyols include glycerine in an amount from about 12 to about 28% by weight and propylene glycol in an amount from about 0 to about 12% by weight. A flavoring agent such as peppermint flavor can be present in the alkaline gel in an amount up to about 0.7% by weight and a coloring agent such as Flamenco Satin Pearl 3500 can be present in the gel in an amount up to about 0.3% by weight.

The alkaline gel is advantageously prepared at low temperatures in a manner which is analogous to the procedure described hereinabove for the preparation of the peroxide gel. In the initial step, formulating amounts of deionized water, glycerine and propylene glycol are sequentially added to and stirred in a mixing vessel. The solution is placed in a freezer and stored for one day at a temperature between about 0° and −14° C. The cold solution is removed from the freezer. Peppermint flavor, N&A anise flavor oil, aloe vera gel decolorized 10X, and Poloxamer 407 (Pluronic F127) are sequentially added to and dissolved in the cold solution with stirring. There is obtained a thickened product which has a white appearance. The thickened product is returned to and stored in the freezer for up to two days. At the end of this time the admixed product is removed from the freezer as a clear liquid with a foam layer that is removed. Coloring agent, Flamenco Satin Pearl 3500, and alkalizing agent, potassium hydroxide, are sequentially added to the clear liquid with stirring. Upon bringing the liquid phase to room temperature, it transforms to a clear gel.

EXAMPLES

The following examples further illustrate ingredients, concentrations and formulations of peroxide gels and alkaline gels which can be used in the practice of this invention. The peroxide gels and the alkaline gels were prepared in accordance with the applicable method and procedure as hereinabove described. The concentration of hydrogen peroxide in the peroxide gel is 15%. In the admixture of the peroxide gel and the alkaline gel, the concentration of hydrogen peroxide is 7.5%.

TABLE I

| Peroxide Gel | Weight Percent | | | |
| --- | --- | --- | --- | --- |
| Ingredients | Ex. 1 | Ex. 2 | Ex. 3 | Ex. 4 |
| Water, deionized | 18.25 | 13.05 | 22.25 | 15.40 |
| Glycerine | 10.00 | 11.00 | 8.00 | 10.00 |
| Propylene glycol | 11.00 | 15.00 | 11.00 | 10.00 |
| Xylitol | 5.00 | 5.00 | 5.00 | 5.00 |
| Hydrogen peroxide (50%) | 30.00 | 30.00 | 30.00 | 30.00 |
| Poloxamer 407 | 25.00 | 26.00 | 23.00 | 29.00 |
| Eugenol | 0.25 | 0.25 | 0.25 | 0.25 |
| Peppermint flavor | 0.50 | 0.70 | 0.50 | 0.35 |
|  | 100.00 | 100.00 | 100.00 | 100.00 |

TABLE II

| Alkaline Gel | Weight Percent | | | |
| --- | --- | --- | --- | --- |
| Ingredients | Ex. 1 | Ex. 2 | Ex. 3 | Ex. 4 |
| Water, deionized | 53.50 | 53.60 | 53.40 | 55.60 |
| Glycerine | 17.00 | 20.00 | 25.00 | 15.00 |
| Propylene glycol | 10.00 | 5.00 | — | 9.00 |
| Poloxamer 407 | 18.00 | 20.00 | 20.00 | 19.00 |
| Peppermint flavor | 0.70 | 0.70 | 0.70 | 0.70 |
| Color: Flamenco Satin Pearl 3500 | 0.30 | 0.20 | 0.40 | 0.20 |
| Potassium hydroxide | 0.50 | 0.50 | 0.50 | 0.50 |
|  | 100.00 | 100.00 | 100.00 | 100.00 |

TABLE III

| Alkaline Gel | Weight Percent | | | |
| --- | --- | --- | --- | --- |
| Ingredients | Ex. 5 | Ex. 6 | Ex. 7 | Ex. 8 |
| Water, deionized | 52.70 | 52.80 | 52.90 | 54.40 |
| Glycerine | 25.00 | 17.00 | 20.00 | 15.00 |
| Propylene glycol | — | 10.00 | 5.00 | 9.00 |
| Poloxamer 407 | 20.00 | 18.00 | 20.00 | 19.00 |
| Peppermint flavor | 0.70 | 0.70 | 0.70 | 0.70 |
| N&A Anise flavor oil | 0.40 | 0.30 | 0.20 | 0.60 |
| Aloe Vera gel decolorized 10X | 0.30 | 0.40 | 0.50 | 0.60 |
| Color: Flamenco Satin Pearl 3500 | 0.40 | 0.30 | 0.20 | 0.20 |
| Potassium hydroxide | 0.50 | 0.50 | 0.50 | 0.50 |
|  | 100.00 | 100.00 | 100.00 | 100.00 |

The peroxide gel and alkaline gel are adapted to be admixed and dispensed into the reservoir system of a dental bleaching tray, such as a custom-fitted dental tray, for application to the teeth to be whitened. In a preferred embodiment, the peroxide gel and alkaline gel are packaged in separate barrels of a double-barrel syringe having a closure cap which is replaced with a static mixer at the time of use. The application of manual force to the syringe actuator, at the time of use, forces the gels into and through the static mixer where the gels are thoroughly mixed and then dispensed into the dental bleaching tray. The system is designed to produce a hydrogen peroxide gel having a moderately high alkaline pH at the time of use and thereby provide a dental gel which has accelerated teeth whitening and bleaching action. The accelerated bleaching action is obtained by treating the teeth with the admixed compositions of this invention for several days at about one-half hour to about one hour or longer per day until the maximum degree of whitening is achieved.

In view of the foregoing descriptions and examples, it will become apparent to those of ordinary skill in the art that equivalent modifications thereof may be made without departing from the spirit and scope for this invention.

That which is claimed is:

1. A two-component dental bleaching system wherein the components are adapted to be admixed and applied to the teeth from a dental bleaching tray for sustained contact, said system consisting essentially of:
   (a) as a first component, a dental peroxide gel having a pH from about 4 to about 7 and consisting essentially of:
       hydrogen peroxide in an amount from about 7 to about 30 wt. %,
       eugenol in an amount from about 0.1 to about 0.5 wt. %,
       poloxamer in an amount to provide a high strength gel,
       gel modifying aliphatic polyol, and
       water to 100%; and
   (b) as a second component, an orally compatible alkaline gel consisting essentially of:
       an alkali metal hydroxide in an amount to provide the alkaline gel with a pH from about 9 to about 13,
       poloxamer in an amount to provide a high strength alkaline gel,
       gel modifying aliphatic polyol, and
       water to 100%;
       whereby the admixing of said components provides a dental bleaching gel of reduced sensitivity and having a pH from about 8.5 to about 11 to thereby increase the rate of release of active oxygen from the peroxide and accelerate the bleaching action.

2. The dental peroxide gel of claim 1 wherein hydrogen peroxide is present in an amount from about 11 to about 22 wt. %; eugenol is present in an amount from about 0.2 to about 0.4 wt. %; the poloxamer is polyoxyethylene polyoxypropylene block copolymer having an average molecular from about 10,000 to about 15,000 and the polyoxyethylene portion thereof constitutes from about 70 to about 80 percent, by weight, of the molecule and is present in an amount from about 18 to about 29 wt. %; and the gel modifying polyol is a member selected from the group consisting of propylene glycol, glycerine, mixtures thereof and equivalents thereto in an amount from about 15 to about 30 wt. %; and
   the alkaline gel of claim 1 wherein the alkali metal hydroxide is potassium hydroxide, the poloxamer is polyoxyethylene polyoxypropylene block copolymer having an average molecular from about 10,000 to about 15,000 and the polyoxyethylene portion thereof constitutes from about 70 to about 80 percent, by weight, of the molecule and is present in an amount from about 18 to about 28 wt. %; and the gel modifying polyol is a member selected from the group consisting of propylene glycol, glycerine and mixtures thereof and equivalents thereto in an amount from about 15 to about 35 wt. %.

3. A method for bleaching teeth which comprises:
   (1) concurrently extruding first and second components of a dental bleaching system through an admixing dispenser and into the reservoir system of a dental bleaching tray,
   (a) said first component defining a dental peroxide gel having a pH from 4 to about 7, and consisting essentially of hydrogen peroxide in an amount from about 7 to about 30 wt. %, eugenol in an amount from about 0.1 to about 0.5 wt. %, poloxamer in an amount to provide a high strength gel, gel modifying aliphatic polyol and water to 100 wt. %, and
   (b) said second component defining an orally compatible alkaline gel having a pH from about 9 to about 13, and consisting essentially of an alkali metal hydroxide in an amount to provide the alkaline gel with a pH from about 9 to about 13, poloxamer in an amount to provide a high strength alkaline gel, gel modifying aliphatic polyol, and water to 100 wt. %,
   (c) whereby the admixture of said first and second components provides a dental bleaching gel having a pH from about 8.5 to about 11 to thereby increase the rate of release of active oxygen and accelerate the bleaching action;
   (2) placing the dental bleaching tray in the oral cavity so as to bring the admixed gel into contact with the teeth to be bleached,
   (3) maintaining said admixed gel in contact with said teeth for up to about one hour or longer per day, and
   (4) repeating steps 1, 2 and 3 for multiple days to thereby bleach the teeth.

4. The method of claim 3 wherein
   (a) the dental peroxide gel consists essentially of:
       hydrogen peroxide in an amount from about 11 to about 22 wt. %,
       eugenol in an amount from about 0.2 to about 0.4 wt. %,
       poloxamer in an amount from about 18 to about 29 wt. % wherein said poloxamer is polyoxyethylene polyoxypropylene block copolymer having an average molecular weight from about 10,000 to about 15,000 and the polyoxyethylene portion thereof constitutes from about 70 to about 80 percent, by weight, of the molecule,
       gel modifying aliphatic polyol selected from the group consisting of propylene glycol, glycerine, mixtures thereof and equivalents thereto in an amount from about 15 to about 30 wt. %, and
       water to 100 wt. % and
   (b) the orally compatible alkaline gel consists essentially of:
       potassium hydroxide in an amount to provide the alkaline gel with a pH from about 10 to about 12,
       poloxamer in an amount from about 18 to about 28 wt. %, wherein said poloxamer is polyoxyethylene polyoxypropylene block copolymer having an average molecular weight from about 10,000 to about 15,000 and the polyoxyethylene portion thereof constitutes from about 70 to about 80 percent, by weight, of the molecule,
       gel modifying aliphatic polyol selected from the group consisting of propylene glycol, glycerine, mixtures thereof and equivalents thereto in an amount from about 15 to about 30 wt. % and
       water to 100 wt. %.

* * * * *